United States Patent [19]

Isaac et al.

[11] Patent Number: 5,466,518
[45] Date of Patent: Nov. 14, 1995

[54] BINDER COMPOSITIONS AND WEB MATERIALS FORMED THEREBY

[75] Inventors: Robert L. Isaac, Bethesda, Md.; Bernard Cohen, Berkeley Lake, Ga.

[73] Assignee: Kimberly-Clark Corporation, Neenah, Wis.

[21] Appl. No.: 107,490

[22] Filed: Aug. 17, 1993

[51] Int. Cl.$^6$ .................................................. D04H 1/58
[52] U.S. Cl. ........................................ 428/288; 428/913
[58] Field of Search ................................. 428/288, 290, 428/913

[56] References Cited

U.S. PATENT DOCUMENTS

| | | | |
|---|---|---|---|
| 3,365,320 | 1/1968 | Minelli | 106/133 |
| 3,526,538 | 9/1970 | Lindemann et al. | 117/140 |
| 3,554,788 | 1/1971 | Fechillas | 117/140 |
| 3,580,253 | 5/1971 | Bernardin | 128/290 |
| 3,890,974 | 6/1975 | Kozak | 128/287 |
| 3,952,347 | 4/1976 | Comerford et al. | 5/335 |
| 4,028,290 | 6/1977 | Reid | 260/17.4 |
| 4,063,995 | 12/1977 | Grossman | 162/112 |
| 4,186,233 | 1/1980 | Krajewski et al. | 428/213 |
| 4,200,558 | 4/1980 | Holst et al. | 260/17 A |
| 4,410,571 | 10/1983 | Korpman | 427/385.5 |
| 4,454,055 | 6/1984 | Richman et al. | 252/194 |
| 4,518,721 | 5/1985 | Dhabhar et al. | 523/120 |
| 4,861,539 | 8/1989 | Allen et al. | 264/204 |
| 4,913,517 | 4/1990 | Arroyo et al. | 350/96.23 |
| 5,013,769 | 5/1991 | Murray et al. | 523/111 |
| 5,056,960 | 10/1991 | Marienfeld | 405/270 |
| 5,225,489 | 7/1993 | Prevorsek et al. | 525/151 |
| 5,248,720 | 9/1993 | Deguchi et al. | 524/444 |

FOREIGN PATENT DOCUMENTS

| | | |
|---|---|---|
| 2005764 | 6/1990 | Canada. |
| 0042259 | 12/1981 | European Pat. Off.. |
| 0164197 | 12/1985 | European Pat. Off.. |
| 0378940A1 | 7/1990 | European Pat. Off.. |
| 0585906A2 | 3/1994 | European Pat. Off.. |
| 63-304082 | 12/1988 | Japan. |
| 05086344 | 4/1993 | Japan. |
| 06057059 | 3/1994 | Japan. |
| 1379660 | 1/1975 | United Kingdom. |
| 2048078 | 12/1980 | United Kingdom. |
| 2246373 | 1/1992 | United Kingdom. |

OTHER PUBLICATIONS

Copy of GB Search Report completed Oct. 7, 1994.
Copy of EP Search Report completed Nov. 11, 1994.
Copy of PCT Search Report mailed Aug. 5, 1994 for PCT counterpart to U.S. Ser. No. 08/046,064.
Copy of European Search Report of Mar. 18, 1994.
*The Condensed Chemical Dictionary*, 10th ed., Gessner G. Hawley, Van Nostrand Reinhold Co., N.Y., N.Y., p. 838, (1981).
*The Condensed Chemical Dictionary*, 10th ed., Gessner G. Hawley, Van Nostrand Reinhold Co., N.Y., N.Y., p. 14, (1981).
*Polymer Yearbook* 3, Richard A. Pethrick, Harwood Academic Publishers, Chur–London–Paris–New York, p. 65, (1986).
"Die Struktur und die Eigenschaften der thixotropen Gele", Von B. S. Kandelaky, *Kolloid–Zeitschrift*, vol. 74 pp. 200–205 (1936).
"Preparation and use of composites swellable by water", *Chemical Abstracts*, vol. 114, No. 12, abstract No. 114:103864m, Mar. 24, 1991.
"The structure and properties of thixotropic gels", *Chemical Abstracts*, vol. 30, No. 19, Oct. 10, 1936.
*Kirk–Othmer Encyclopedia of Chemical Technology*, 3rd ed., vol. 5, pp. 118–163, John Wiley & Sons, N.Y.–Chichester–Brisbane & Toronto, (1979).
*Kirk–Othmer Encyclopedia of Chemical Technology*, 3rd ed., vol. 21, pp. 492–505, John Wiley & Sons, N.Y.–Chichester–Brisbane & Toronto, (1981).
Lisa Brannon–Peppas and Ronald S. Harland (eds.), *Absorbent Polymer Technology*, Elsevier, 1990, pp. 3–22.
BF Goodrich Specialty Polymers & Chemicals Division, *HyStretch*™ *Elastomer Emulsions*, Doc. No. MSD90.534, Nov. 2, 1990.
Eastman Chemicals, *Eastman AQ® Polymers Properties and Applications*, Publication No. GN–389B, May 1990, pp. 2–27.
Hoechst Celanese Corporation, *Material Safety Data Sheet*, MSDS No. 1101750318, Feb. 7, 1992, pp. 1–3.
*Kolloid–Zeitschrift*. vol. 74, 1936, pp. 200–205.
Paul C. Hiemenz, *Principles of Colloid and Surface Chemistry*, Marcel Dekker, Inc., 1986, pp. 782–783.

*Primary Examiner*—Christopher W. Raimund
*Attorney, Agent, or Firm*—Joseph P. Harps

[57] ABSTRACT

The present invention is directed toward a fibrous web having improved strength characteristics which, in the presence of water, rapidly disintegrates when subjected to standardized agitation testing. The web includes a plurality of fibers joined together by a binder. The binder makes up from about 0.20 to about 15 percent of the dry weight of the web. The binder is formed from a blend of from about 10 to about 40 weight percent of a water dispersible, high molecular weight amorphous polyester having one or more ionic substituents attached thereto; from about 10 to about 40 weight percent of an elastomeric latex emulsion; from about 20 to about 40 weight percent of a xerogellant; and from about 5 to about 20 weight percent of a plasticizing agent. The fibrous web is useful in the formation of disposable diapers and feminine care products which may be flushed down the toilet.

19 Claims, No Drawings

BINDER COMPOSITIONS AND WEB MATERIALS FORMED THEREBY

RELATED APPLICATIONS

U.S. patent application Ser. No. 07/997,797 entitled *"Hydrodisintegratable Material and Products Formed Thereby"* filed on Dec. 29, 1992, pending in the names of Messers. Cohen, Jameson and Isaac and U.S. patent application Ser. No. 08/046,064 entitled *"Self Sealing Film"* filed on Apr. 12, 1993 in the names of Messers. Isaac, Cohen and Jameson, pending.

1. Field of the Invention

The field of the present invention is that of binder compositions for use in the formation of coherent fibrous web materials which have the ability to rapidly fall apart or disintegrate into a collection of generally individual fibers in an aqueous medium when subjected to agitation.

2. Background of the Invention

For many years the problem of disposability has plagued the industries which provide disposable diapers, incontinent garments and feminine care products. While much headway has been made in addressing this problem, one of the weak links has been the inability to create an economical coherent fibrous web which will readily dissolve or disintegrate in water. See, for example, U.K. patent disclosure 2,241,373 and U.S. Pat. No. 4,186,233. Without such a product, the ability of the user to dispose of the product by flushing it down the toilet is greatly reduced if not eliminated. Furthermore, the ability of the product to disintegrate in a landfill is quite limited because a large portion of the components of the product, which may well be biodegradable or photodegradable, are encapsulated in plastic which degrades over a long period of time, if at all. Accordingly, if the plastic at least disintegrated in the presence of water, the internal components could degrade as a result of the rupture of the plastic encapsulation.

In prior U.S. patent application Ser. No. 07/997,797 entitled *"Hydrodisintegratable Material and Products Formed Thereby"* which was filed on Dec. 29, 1992, a composition is described which has the ability to disintegrate in the presence of water. Thin material can be used to form plastic films which disintegrate in the presence of water. However, those in the art have also been searching for a fibrous material or web (as compared to a film) which has the ability to disintegrate in the presence of water.

Disposable diapers, feminine care products and adult incontinent care products generally usually have a body side liner which must rapidly pass fluids such as, for example, urine or menses, so that the fluid may be absorbed by the absorbent core of the product. Typically, the body side liner is a cohernet fibrous web which desirably possesses a number of characteristics such as softness and flexibility. The fibrous webs of the body side liner material are typically formed by wet or dry (air) laying a generally random plurality of fibers and joining them together to form a coherent web with a binder. Past binders have preformed this function well. From an environmental standpoint it might be stated that the past binders have performed this function too well in that the binders tended not to degrade and thus the liner remained intact. This action severely hampered any environmental degradation of the disposable product.

Wet and dry (air) laid webs which disintegrate in the presence of water are generally known in the art. However, a problem with these webs is that they lack strength and cannot be effectively utilized in a consumer product because of their proclivity to rapidly fall apart. Thus, an impression of a "cheap" product can result in the mind of the consumer. Accordingly, a desirable attribute which those of skill in the art have been seeking was to discover a binder composition which increased the strength of wet and dry (air) laid webs but still allow the bonded coherent web to rapidly disintegrate to a group of generally individual fibers once it was placed in an aqueous environment. In attempting to design a porous, fibrous, web resort was first had to the teachings of the aforesaid '797 application. However, the use of that material as a binder resulted in a generally stiff material which did not appear to be desirable.

OBJECTS OF THE INVENTION

Accordingly, it is a general object of the present invention to provide a coherent fibrous web having improved strength characteristics which readily falls apart or disintegrates into a collection of generally individual fibers when subjected to agitation in the presence of water.

Another general object of the present invention is to provide a process for forming such a coherent fibrous web.

Yet another general object of the present invention is to provide a binder for use in the formation of such coherent fibrous webs.

Still further objects and the broad scope of applicability of the present invention will become apparent to those of skill in the art from the details given hereinafter. However, it should be understood that the detailed description of the presently preferred embodiment of the present invention is given only by way of illustration because various changes and modifications well within the spirit and scope of the invention will become apparent to those of skill in the art in view of the following description.

SUMMARY OF THE INVENTION

In response to the foregoing problems and difficulties the present invention is directed toward a hydrodisintegratable coherent fibrous web having improved strength characteristics. The web includes a plurality of fibers joined together by a binder. The binder makes up from about 0.20 to about 15 percent of the dry weight of the web. The binder is formed from a blend of from about 10 to about 40 weight percent of a water dispersible polymer; from about 10 to about 40 weight percent of an elastomeric latex emulsion; from about 20 to about 40 weight percent of a xerogellant; and from about 5 to about 20 weight percent of a plasticizing agent. The fibrous web is useful in the formation of disposable diapers and feminine care products which may be flushed down the toilet.

For example, the hydrodisintegratable fibrous web may include from about 20 to about 40 weight percent of the water dispersible polymer; from about 20 to about 40 weight percent of the elastomeric latex emulsion; from about 20 to about 40 weight percent of the xerogellant; and from about 10 to about 20 weight percent of the plasticizing agent. More particularly, the hydrodisintegratable fibrous web may include from about 20 to about 35 weight percent of the water dispersible polymer; from about 20 to about 35 weight percent of the elastomeric latex emulsion; from about 20 to about 35 weight percent of the xerogellant; and from about 10 to about 15 weight percent of the plasticizing agent. Even more particularly, the hydrodisintegratable fibrous web may include from about 25 to about 30 weight percent of the water dispersible polymer; from about 25 to about 30 weight percent of the elastomeric latex emulsion; from about 25 to about 30 weight percent of the xerogellant; and from about 10 to about 15 weight percent of the plasticizing agent.

In some embodiments the hydrodisintegratable fibrous web is formed by air-laying or wet-laying processes.

In some embodiments the water dispersible polymer may be selected from the group including high molecular weight amorphous polyesters having one or more ionic substituents attached thereto. In other embodiments, the water dispersible polymer may be selected from the group including acrylic polymers, polyoxides, vinyl polymers, cellulose derivatives, starch derivatives, polysaccahrides, proteins and copolymers thereof.

In some embodiments the elastomeric latex emulsion may include about 50% latex, about 50% water, less than about 0.01% acrylamide, less than about 1.0% ammonium hydroxide, less than about 0.01% ethyl acrylate, less than about 0.1% formaldehyde and less than about 0.0025% N-methylolacrylamide.

In some embodiments the xerogellant may be selected from the group including sodium carboxymethyl cellulose, derivatives of sodium carboxymethyl cellulose, poly(acrylic acid) salts, poly(ethylene oxide), acrylonitrile-grafted starch, hydrolyzed polyacrylonitrile, poly(vinyl alcohol-sodium acrylate), polyisobutylene-co-disodium maleate).

In some embodiments the plasticizing agent may be selected from the group including glycerin, sorbitol, glucidol, sucrose, ethylene glycol, propylene glycol, diethylene glycol, polyethylene glycol, acid amide, dimethyl acetamide, dimethyl sulfoxide, methyl pyrrolidene and tetramethylene sulfone.

A desirable attribute of the hydrosisintegratable fibrous web of the present invention is that the tensile strength of the web is greater than the tensile strength of the same web formed without the binder. For example, the tensile strength of the hydrodisintegratable fibrous web may be at least 25 percent greater than the tensile strength of a like web not containing the binder. More particularly, the tensile strength of the hydrodisintegratable fibrous web may be at least 100 percent greater than the tensile strength of a like web not containing the binder. Even more particularly, the tensile strength of the hydrodisintegratable fibrous web may be at least 500 percent greater than the tensile strength of a like web not containing the binder. Yet even more particularly, the tensile strength of the hydrodisintegratable fibrous web may be at least 1,000 percent greater than the tensile strength of a like web not containing the binder.

In some embodiments the hydrodisintegratable web includes at least 85 percent, by weight, of the fibers and from about 0.20 to about 15 percent, by weight, of the binder. More particularly, the hydrodisintegratable web may include at least 90 percent, by weight, of fibers and from about 0.20 to about 10 percent, by weight, of the binder. Even more particularly, the hydrodisintegratable web includes at least 95 percent, by weight, of fibers and from about 0.20 to about 5 percent, by weight, of the binder.

A desirable attribute of the hydrodisintegratable web is that it is adapted to rapidly disintegrate in distilled water when subjected to agitation. For example, the hydrodisintegratable web may be adapted to disintegrate in distilled water in 30 seconds or less when subjected to agitation.

The present invention is also directed toward a process for forming a hydrodisintegratable fibrous web adapted to disintegrate in distilled water in 30 seconds or less when subjected to agitation. The process includes the steps of: (1) providing a plurality of generally randomly arranged fibers in a mat-like configuration; and (2) applying a binder solution onto the fibers to form a coherent fibrous web, the binder solution comprising from about 0.20 to about 15 percent of the dry weight of the web. In this process the applied binder solution includes: (a) from about 10 to about 40 weight percent of a water dispersible polymer; (b) from about 10 to about 40 weight percent of an elastomeric latex emulsion; (c) from about 20 to about 40 weight percent of a xerogellant; and (d) from about 5 to about 20 weight percent of a plasticizing agent.

In some embodiments the randomly arranged fibers may be provided by an air-laying process. Alternatively, the randomly arranged fibers may be provided by a wet-laying process.

In some embodiments the binder may be applied by spraying. Alternatively, the binder may be applied by dipping.

The present invention is also directed toward the binder compositions themselves. Such binder compositions may be desirably utilized wherever it is desired for a bound material to subdivide or break apart into smaller units when subjected to agitation in an aqueous medium.

DEFINITIONS

As used herein, the term "xerogellant" refers to a material which, when in a substantially dry state, has the ability to spontaneously imbibe at least about twenty (20) times its own weight in aqueous fluid. Importantly, the xerogellant should have the ability to generally retain its original identity after it has imbibed the fluid. For example, a bead, fiber or film formed from a xerogellant will still be recognizable as such after having imbibed the fluid.

As used herein, the term "water dispersible polymer" refers to a polymeric material which is capable of forming a dispersion in an aqueous medium at ambient temperature.

As used herein, the term "plasticizing agent" refers to an organic compound which, when added to a high polymer, may increase the ease of processing the high polymer or increase the toughness and flexibility of the high polymer after processing. A plasticizing agent may be able to accomplish all of these.

As used herein the term "elastomeric latex emulsion" refers to a stable mixture of water and latex held in suspension by small percentages of surface active agent(s), called emulsifier(s).

As used herein, the term "hydrodisintegratable coherent fibrous web" refers to a coherent web material which, when subjected to agitation in an aqueous medium at ambient temperature, will fall apart or break-up into a collection of fibers so that the web effectively ceases to exist.

As used herein, the term "shake test" refers to a test procedure which is used to measure the rate at which a web falls apart in distilled water. The test is conducted as follows: (1) a 2 inch by 2 inch sample is cut and weighed; (2) the sample is placed in a 125 milliliter nalgene Erhlenmeyer flask having a screw top lid and 100 milliliters of distilled water is added to the flask; (3) the flask is placed in a Burrell Model 75 Wrist Action Shaker manufactured by the Burrell Corp. of Pittsburg, Pa. and shaken at maximum agitation for thirty (30) seconds; (4) if the sample does not totally disintegrate, collect the remaining pieces of the sample and record their number and size; (5) calculate the percent remaining undispersed for the sample by dividing the weight of any remaining pieces by the original weight of the sample and multiplying by 100.

As used herein the term "wet-laid" is equivalent to the term "wet-forming" which indicates a process such as, for example, paper making, where a nonwoven material is formed from an aqueous suspension of fibers. Exemplary products which can be made by wetlaid process include paper, artificial leather, backing for sandpaper and face masks.

As used herein the term "air-laid" is equivalent to the term "air forming" which indicates a process in which air is used to separate and move fibers to fashion a web. Exemplary products which can be made by air-laying processes generally include high mass low density materials such as wipers, pads and bedding mats. Exemplary air-laying processes include corforming, meltblowing and spunbonding.

DETAILED DESCRIPTION OF THE INVENTION

The binder composition of the present invention is formed by placing a xerogellant, desirably in powder form, in an appropriately sized container and adding sufficient water so that the xerogellant is fully hydrated (swollen) to a gel. This step may take up to an hour or more depending upon the xerogellant used. While any material meeting the definition of a xerogellant may be utilized, exemplary xerogellants include sodium carboxymethyl cellulose, derivatives of sodium carboxymethyl cellulose, poly(acrylic acid) salts, (ethylene oxide), acrylonitrile-grafted starch, hydrolyzed polyacrylonitrile, poly(vinyl alcohol-sodium acrylate) and polyisobutylene-co-disodium maleate. One xerogellant is a starch grafted sodium polyacrylate which may be obtained from Hoechst Celanese Corporation under the trade designation Sanwet IM5000P.

Once the xerogellant has completely swelled, it is transferred to a blender, for example a Waring blender, and mixed at a high speed until it is in a liquified form. Those in the art will recognize that it may be necessary to add a small amount of additional water to achieve a liquified state. It is to the liquified xerogellant that the water dispersible polymer, the elastomeric latex emulsion and the plasticizing agent are added.

Next, the water dispersible polymer, the elastomeric latex emulsion and the plasiticzing agent are added to the liquified xerogellant and all four components are thoroughly mixed at low speed in, for example, a blender. Typically additional water is added at this stage to assist in the blending operation. Desirably, the water dispersible polymer may be added to the hydrated xerogellant as an aqueous dispersion.

While any water dispersible polymer may be utilized, exemplary water dispersible polymers include such polymers chosen from the group including relatively high molecular weight amorphous polyesters that disperse directly in water without the asistance of organic cosolvents, suractants, or amines. This water dispersibiity is attributable, in large part, to the presence of ionic substituents attached to the polymer chain, illustrated below.

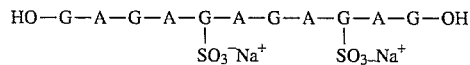

A=an aromatic dicarboxylic acid moiety
G=an aliphatic or cycloaliphatic glycol residue
—OH=hydroxy end groups
While only two of the aromatic dicarboxylic acid moieties shown above have sodiosulfo ($SO_3^-Na^+$) substituents, on the average, there are five to eight ionic sodiosulfo substituents per molecule.

This type of polymer is available form the Eastman Kodak Co. of Rochester, N.Y. under the trade designation Eastman AQ. In particular, Eastman AQ 55D and AQ 38D. The "D" represents the fact that the polymer is in a dispersed form. The number refers to the dry glass transition temperature, in degrees Centigrade, of the polymer.

Alternatively, the water dispersible polymer may be selected from the group including acrylic polymers, polyoxides, vinyl polymers, cellulose derivatives, starch derivatives, polysaccahrides, proteins and copolymers thereof.

While any suitable elastomeric latex emulsion may be utilized, exemplary elastomeric latex emulsions may be obtained from the B. F. Goodrich Co., Specialty Polymers & Chemicals Division under the trade designation HyStretch, for example HyStretch V-60. HyStretch V-60 elastomeric latex emulsions typically are a blend of about 50% latex, about 50% water, less than about 0.01% acrylamide, less than about 1.0% ammonium hydroxide, less than about 0.01% ethyl acrylate, less than about 0.1% formaldehyde and less than about 0.0025% N-methlolacrylamide. U.S. Pat. No. 5,056,960 to Marienfeld has described HyStretch V-60 as an aqueous dispersion based on an elastomeric, fully saturated, acrylic terpolymer.

While any suitable plasticizing agent may be utilized, exemplary plasticizing agents include glycerin, sorbitol, glucidol, sucrose, ethylene glycol, propylene glycol, diethylene glycol, polyethylene glycol, acid amides, dimethyl acetamide, dimethyl sulfoxide, methyl pyrrolidene and tetramethylene sulfone. One exemplary plasticizing agent is glycerin which may be obtained from Fischer Scientific of Fairtown, N.J., under the trade designation G-33-1.

The resultant binder composition contains: (1) from about 10 to about 40 weight percent of the water dispersible polymer; (2) from about 10 to about 40 weight percent of the elastomeric latex emulsion; (3) from about 20 to about 40 weight percent of the xerogellant; and (4) from about 5 to about 20 weight percent of the plasticizing agent in an aqueous solution. For example, the resultant binder composition may contain: (1) from about 20 to about 40 weight percent of the water dispersible polymer; (2) from about 20 to about 40 weight percent of the elastomeric latex emulsion; (3) from about 20 to about 40 weight percent of the xerogellant; and (4) from about 10 to about 20 weight percent of the plasticizing agent in an aqueous solution. More particularly, the resultant binder composition may contain: (1) from about 20 to about 35 weight percent of the water dispersible polymer; (2) from about 20 to about 35 weight percent of the elastomeric latex emulsion; (3) from about 20 to about 35 weight percent of the xerogellant; and (4) from about 10 to about 15 weight percent of the plasticizing agent in an aqueous solution. Even more particularly, the resultant binder composition may contain: (1) from about 25 to about 30 weight percent of the water dispersible polymer; (2) from about 25 to about 30 weight percent of the elastomeric latex emulsion; (3) from about 25 to about 30 weight percent of the xerogellant; and (4) from about 10 to about 15 weight percent of the plasticizing agent in an aqueous solution.

As will be discussed in more detail hereinafter, the binder composition may be applied by either spraying processes or dipping processes. Generally speaking, the percent of the four components in the aqueous solution should be tailored to the application process which is to be utilized. For example, when it is desired to apply the binder composition by dipping, the percent of the four components in solution is usually greater than 1 percent. More particularly, the percent of the four components in solution may be greater than 1.1 percent. Even more particularly, the percent of the four components in solution may be greater than 1.25 percent if the binder composition is to be applied by dipping. Yet even more particularly, the percent of the four components in solution may be greater than 2 percent if the binder composition is to be applied by dipping.

If the binder composition is to be applied by spraying processes, the percent of the four components in solution may be less than 1 percent. For example, the percent of the four components in solution may be less than 0.50 percent if the binder composition is to be applied by spraying. Even more particularly, the percent of the four components in solution may be less than 0.25 percent if the binder composition is to be applied by spraying.

Once the binder composition has been formulated as described above it is transferred to an appropriate spraying mechanism or dipping trough, depending upon the method of application of the composition.

At this point a coherent wet-laid or dry-laid (air-laid) fibrous web prepared by conventional methods is provided. These webs are coherent in that they are self-supporting and may be relatively easily handled so long as they are handled with care. Moreover, these conventional webs will disintegrate or fall apart when placed in water and aggitated. However, these conventional webs have very low tensile strength and will readily tear apart.

Application of the binder by either the spraying or dipping process is then carried out in conventional manner.

Once the wet-laid or dry (air) laid web has had the binder applied it is allowed to dry in conventional manner. Once dry, the coherent webs exhibit improved tensile strength when compared to the tensile strength of the untreated wet-laid or dry-laid webs. For example, the tensile strength of the fibrous web may be increased by at least 25 percent as compared to the tensile strength of the untreated web not containing the binder. More particularly, the tensile strength of the fibrous web may be increase by at least 100 percent as compared to the tensile strength of the untreated web not containing the binder. Even more particularly, the tensile strength of the fibrous web may be increased by at least 500 percent as compared to the tensile strength of the untreated web not containing the binder. Yet even more particularly, the tensile strength of the fibrous web may be increase by at least 1,000 percent as compared to the tensile strength of the untreated web not containing the binder.

A desirable feature of the present invention is that the improvement in tensile strength is effected where the amount of binder present, "add-on", in the resultant hydrodisintegratable fibrous web represents only a small portion, by weight, of the entire web. For example, the binder components typically are from about 0.20 to about 15 percent, by weight, of the dry web. More particularly, the binder components may be from about 0.20 to about 10 percent, by weight, of the dry web. Even more particularly, the binder components may be from about 0.30 to about 5 percent, by weight, of the web.

Importantly, the resultant coherent fibrous webs have the ability to rapidly "fall apart" or disintegrate when placed in water and aggitated. Thus, this material may be effectively utilized in disposable products which may be placed in a toilet and flushed away.

In some embodiments it may be desirable to employ various additives such as antioxidants, antistatic agents, blowing agents, compatibilizers, flame retardants, heat stabilizers, impact modifiers, lubricants, ultraviolet stabilizers, processing aids, surfactants, dispersants, slip agents, etc., as fabricating agents or as modifiers depending on the specific properties which would be desirable to have in the final product.

The use of surfactants can further enhance the rate of hydrodisintegration of the coherent fibrous web. Exemplary surfactants which can be utilized in the invention are (1) anionic surfactants such as carboxylic acids and salts, sulfonic acids and salts, sulfuric acid esters and salts, phosphoric and polyphosphoric acid esters and salts; (2) nonionic surfactants such as ethoxylated alcohols, ethoxylated alhylphenols, ethoxylated carboxylic esters and ethoxylated carboxylic amides; (3) cationic surfactants such as oxygen free amines, oxygen containing amines, amide linked amines and quaternary ammonium salts; and (4) amphoteric surfactants such as imidazolinium derivatives, amino acids and their derivatives in which the nitrogen atom is protonated and alkylketaimes.

The surfactants may be added so that they form from at least about 0.01 to about 0.10 weight percent of the coherent fibrous web. For example, the surfactants may form from at least about 0.03 to about 0.08 weight percent of the coherent fibrous web. More particularly, the surfactants may form from at least about 0.05 to about 0.06 weight percent of the coherent fibrous web.

Those of skill in the art will readily recognize that the hydrodisintegratable coherent web may be formed by other methods.

The invention will now be described with respect to certain specific embodiments thereof.

EXAMPLES

Three binder compositions were prepared in accordance with the present invention. One to be applied by spraying on wet-laid webs, one to be applied to wet-laid webs by dipping and one to be applied onto air-laid webs by dipping.

For the spraying application, about 0.1 gram of xerogellant, Sanwet IM5000P, was added to a 100 milliliter beaker with 80 milliliters of water. The xerogellant was allowed to swell (hydrate) for about one (1) hour. Thereafter, the hydrated xerogellant was transferred to a Waring blender 7011 model 31BL92 and mixed at high speed for about one (1) minute until the gel was liquified. At this point seventy (70) additional milliliters of water, 0.4 grams of water dispersible polymer (AQ55D), 0.225 grams of elastomeric latex emulsion (HyStretch V-60) and 0.045 grams of plasticizing agent (Glycerin) were added. Because the AQ55D is only 25% solids, only 0.1 gram of these solids were actually added. Because the HyStretch V-60 is only 50% solids, only 0.11 gram of these solids were actually added. Thus, the resultant binder composition had 0.355 grams of total solids in 150 milliliters of water. This is a 0.24% solution.

For the dipping of wet-laid webs application, about 1 gram of xerogellant, Sanwet IM5000P, was added to a 100 milliliter beaker with 80 milliliters of water. The xerogellant was allowed to swell (hydrate) for about one (1) hour. Thereafter, the hydrated xerogellant was transferred to a Waring blender 7011 model 31BL92 and mixed at high speed for about one (1) minute until the gel was liquified. At this point one hundred and seventy (170) additional milliliters of water, 4 grams of water dispersible polymer (AQ55D), 2 grams of elastomeric latex emulsion (HyStretch V-60) and 0.45 gram of plasticizing agent (Glycerin) were added. Because the AQ55D is only 25% solids, only 1 gram of these solids were actually added. Because the HyStretch V-60 is only 50% solids, only 1 gram of these solids were actually added. Thus, the resultant binder composition had 3.45 grams of total solids in 250 milliliters of water. This is a 1.38% solution.

For the dipping of air-laid webs application, about 0.5 gram of xerogellant, Sanwet IM5000P, was added to a 100 milliliter beaker with 80 milliliters of water. The xerogellant was allowed to swell (hydrate) for about one (1) hour. Thereafter, the hydrated xerogellant was transferred to a Waring blender 7011 model 31BL92 and mixed at high speed for about one (1) minute until the gel was liquified. At this point eighty (80) additional milliliters of water, 2 grams of water dispersible polymer (AQ55D), 1 gram of elastomeric latex emuslion (HyStretch V-60) and 0.225 gram of plasticizing agent (Glycerin) were added. Because the AQ55D is only 25% solids, only 0.5 gram of these solids were actually added. Because the HyStretch V-60 is only 50% solids, only 0.5 gram of these solids were actually added. Thus, the resultant binder composition had 1.724 grams of total solids in 160 milliliters of water. This is a 1.1% solution.

In each case the entire solution was mixed on low speed in the blender for about thirty (30) seconds.

In the spraying application the resultant solution was transferred to a small amber bottle attached to a Chromist (trademark) sprayer model number 51901 sold by Gelman Sciences of Ann Arbor, Mich. for spray application.

In the dipping applications, the resultant solution was poured into a pyrex dish and covered until the samples were treated.

The wet-laid webs used in these experiments were generally composed of three (3) denier, one-half inch length polyester obtained from Mini Fibers Corp. of Johnson, Texas and Abaca pulp. More specifically, about 60%, by weight, polyester, about 40 %, by weight, Abaca pulp and about 0.125%, by weight, of a wet strength resing (Parez NC631) obtained from American Cyanamid Corp. of Wayne N.J. These webs were manufactured by the Kimberly-Clark Corp at its Lee Mill in Lee Mass.. Their basis weight was approximately 27 grams per square meter.

The air-laid webs used in these experiments were generally composed of 100% polyester fibers obtained from the Mini Fiber Corp. of Johnson, Tex. with a polyvinyl alcohol binder. The PVOH binder represented about 0.5%, by weight, add-on of the webs. The binder is available under the trade designation grade 523 Airvol from Air Products & Chemicals, Inc. of Allentown, Pa. More specifically, the polyester fibers had an average denier of three (3) and an average lenght of one-half (½) inch. The webs were made at Clemson Univ., Clemson S.C. on Rando web air laying equipment. Their basis weight was approximately 45 grams per square meter.

Samples of the webs to have binder applied in accordance with the present invention were cut to three (3) inch by seven (7) size. Each sample was weighed before binder application and after the binder had been applied and the web dried. Drying was accomplished by hand blotting and the sample being hung in a hood at ambient temperature overnight.

If the binder application was accomplished by dipping the airlaid webs were supported by a screen during the actual dipping phase. In the case of spraying, the webs were sprayed directly.

The dried webs were tested for machine direction (MD) tensile strength using an Instron Materials Testing Machine model number 1122. The guage length was set at three (3) inches and the cross head speed was twelve 12 inches per minute. Peak Load was recorded for each sample tested, including the control webs. Percent increase in strength was calculated as: (treated tensile strength—control tensile strength divided by control tensile strength) times 100. The results of these examples are recorded in Table I, below.

TABLE I

| SAMPLE WEB | TYPE OF APPLICATION | BINDER CONC. (percent) | PERCENT ADD ON (by wt.) | CONTROL TENSILE (grams) | TREATED TENSILE (grams) | INCREASE IN STRENGTH (percent) |
|---|---|---|---|---|---|---|
| WETLAID | SPRAY | .24 | 0.30 | 1295 | 1755 | 35.52 |
| WETLAID | SPRAY | .24 | 1.30 | 1295 | 2506 | 93.51 |
| WETLAID | SPRAY | .24 | 1.60 | 1295 | 2983 | 130.35 |
| WETLAID | SPRAY | .24 | 1.90 | 1295 | 2019 | 55.91 |
| WETLAID | DIP SATURATION | 1.38 | 4.90 | 1295 | 3293 | 154.29 |
| WETLAID | DIP SATURATION | 1.38 | 5.10 | 1295 | 5314 | 310.35 |
| WETLAID | DIP SATURATION | 1.38 | 5.90 | 1295 | 5763 | 345.02 |
| WETLAID | DIP SATURATION | 1.38 | 9.90 | 1295 | 6860 | 429.73 |
| WETLAID | DIP SATURATION | 1.38 | 7.50 | 1295 | 5243 | 304.86 |
| AIRLAID | DIP SATURATION | 1.10 | 6.90 | 160.8 | 1825 | 1034.95 |
| AIRLAID | DIP SATURATION | 1.10 | 7.50 | 160.8 | 1461 | 808.58 |
| AIRLAID | DIP SATURATION | 1.10 | 2.20 | 160.8 | 1340 | 733.33 |
| AIRLAID | DIP SATURATION | 1.10 | 13.50 | 160.8 | 2047 | 1173.01 |

All of the samples were also subjected to the shake test as defined above. All of the samples formed in accordance with the present invention, fell apart into generally individual fibers in less than thirty (30) seconds. While the control samples had accomplished this objective in about ten (10) seconds, the significant improvement in tensile strength of the samples of the present invention as compared to that of the control samples allows the samples of the present invention to be utilized in commercial applications. Moreover, the fact that the samples of the present invention had fallen apart in under thirty seconds is believed to make them suitable for use in products which may be flushed down the toilet.

It is to be understood that variations and modifications of the present invention may be made without departing from the scope of the invention. It is also to be understood that the scope of the present invention is not to be interpreted as limited to the specific embodiments disclosed herein, but only in accordance with the appended claims when read in light of the foregoing disclosure.

What is claimed is:

1. A fibrous web adapted to disintegrate in distilled water in 30 seconds or less when subjected to agitation, the web comprising:

a plurality of fibers; and from about 0.20 to about 15 percent, by weight, of a binder joining the fibers together, the binder comprising:

from about 10 to about 40 weight percent of a water dispersible polymer selected from the group consisting of high molecular weight amorphous polyester having one or more ionic substituents attached thereto;

from about 10 to about 40 weight percent of an elastomeric latex emulsion;

from about 20 to about 40 weight percent of a xerogellant; and from about 5 to about 20 weight percent of a plasticizing agent.

2. The hydrodisintegratable fibrous web of claim 1, wherein the fibers are air-laid fibers.

3. The hydrodisintegratable fibrous web of claim 1, wherein the fibers are wet-laid fibers.

4. The hydrodisintegratable fibrous web of claim 1, wherein the elastomeric latex emulsion comprises about 50% latex, about 50% water, less than about 0.01% acrylamide, less than about 1.0% ammonium hydroxide, less than about 0.01% ethyl acrylate, less than about 0.1% formaldehyde and less than about 0.0025% N-methylolacrylamide.

5. The hydrodisintegratable fibrous web of claim 1, wherein the xerogellant is selected from the group consisting of sodium carboxymethyl cellulose, derivatives of sodium carboxymethyl cellulose, poly(acrylic acid) salts, poly(ethylene oxide), acrylonitrile-grafted starch, hydrolyzed polyacrylonitrile, poly(vinyl alcohol-sodium acrylate) and, polyisobutylene-co-disodium maleate).

6. The hydrodisintegratable fibrous web of claim 1, wherein the plasticizing agent is selected from the group consisting of glycerin, sorbitol, glucidol, sucrose, ethylene glycol, propylene glycol, diethylene glycol, polyethylene glycol, acid amide, dimethyl acetamide, dimethyl sulfoxide, methyl pyrrolidene and tetramethylene sulfone.

7. The hydrodisintegratable fibrous web of claim 1, wherein the binder comprises:

from about 20 to about 40 weight percent of the water dispersible polyester;

from about 20 to about 40 weight percent of the elastomeric latex emulsion;

from about 20 to about 40 weight percent of the xerogellant; and from about 10 to about 20 weight percent of the plasticizing agent.

8. The hydrodisintegratable fibrous web of claim 1, wherein the binder comprises:

from about 20 to about 35 weight percent of the water dispersible polyester;

from about 20 to about 35 weight percent of the elastomeric latex emulsion;

from about 20 to about 35 weight percent of a xerogellant; and from about 10 to about 15 weight percent of the plasticizing agent.

9. The hydrodisintegratable fibrous web of claim 1, wherein the binder comprises:

from about 25 to about 30 weight percent of the water dispersible polyester;

from about 25 to about 30 weight percent of the elastomeric latex emulsion;

from about 25 to about 30 weight percent of the xerogellant; and from about 10 to about 15 weight percent of the plasticizing agent.

10. The hydrodisintegratable fibrous web of claim 1, wherein the tensile strength of the fibrous web is at least 25 percent greater than the tensile strength of a like web not containing the binder.

11. The hydrodisintegratable fibrous web of claim 1, wherein the tensile strength of the fibrous web is at least 100 percent greater than the tensile strength of a like web not containing the binder.

12. The hydrodisintegratable fibrous web of claim 1, wherein the tensile strength of the fibrous web is at least 500 percent greater than the tensile strength of a like web not containing the binder.

13. The hydrodisintegratable fibrous web of claim 1, wherein the tensile strength of the fibrous web is at least 1,000 percent greater than the tensile strength of a like web not containing the binder.

14. The hydrodisintegratable fibrous web of claim 1, wherein the web comprises at least about 90 percent, by weight, of said plurality of fibers and from about 0.20 to about 10 percent, by weight, of said binder.

15. The hydrodisintegratable fibrous web of claim 1, wherein the web comprises at least about 95 percent, by weight, of said plurality of fibers and from about 0.30 to about 5 percent, by weight, of said binder.

16. A fibrous web adapted to disintegrate in distilled water in 30 seconds or less when subjected to agitation, the web comprising:

a plurality of fibers; and from about 0.20 to about 15 percent, by weight, of a binder joining the fibers together, the binder comprising:

from about 10 to about 40 weight percent of a water dispersible high molecular weight amorphous polyester having one or more ionic substituents attached thereto;

from about 10 to about 40 weight percent of an elastomeric latex emulsion;

from about 20 to about 40 weight percent of starch grafted sodium polyacrylate; and from about 5 to about 20 weight percent of glycerin.

17. The hydrodisintegratable fibrous web of claim 16, wherein the binder comprises:

from about 20 to about 40 weight percent of the water dispersible polyester;

from about 20 to about 40 weight percent of the elastomeric latex emulsion;

from about 20 to about 40 weight percent of starch grafted sodium polyacrylate; and from about 10 to about 20 weight percent of glycerin.

18. The hydrodisintegratable fibrous web of claim 16, wherein the binder comprises:

from about 20 to about 35 weight percent of the water dispersible polyester;

from about 20 to about 35 weight percent of the elastomeric latex emulsion;

from about 20 to about 35 weight percent of starch grafted sodium polyacrylate; and from about 10 to about 15 weight percent of glycerin.

19. A fibrous web adapted to disintegrate in distilled water in 30 seconds or less when subjected to agitation, the web comprising:

a plurality of fibers; and from about 0.20 to about 15 percent, by weight, of a binder joining the fibers together, the binder comprising:

from about 25 to about 30 weight percent of a water dispersible high molecular weight amorphous polyester having one or more ionic substituents attached thereto;

from about 25 to about 30 weight percent of an elastomeric latex emulsion;

from about 25 to about 30 weight percent of starch grafted sodium polyacrylate; and from about 10 to about 15 weight percent of glycerin.

\* \* \* \* \*